US010588991B1

(12) United States Patent
Dornau

(10) Patent No.: US 10,588,991 B1
(45) Date of Patent: Mar. 17, 2020

(54) DISINFECTANT POUCH WITH FLUID CONTROL

(71) Applicant: Odorstar Technology, LLC, Davie, FL (US)

(72) Inventor: Peter Dornau, Davie, FL (US)

(73) Assignee: Odorstar Technology, LLC, Davie, FL (US)

( * ) Notice: Subject to any disclaimer, the term of this patent is extended or adjusted under 35 U.S.C. 154(b) by 0 days.

(21) Appl. No.: 16/504,766

(22) Filed: Jul. 8, 2019

(51) Int. Cl.
*A61L 2/20* (2006.01)
*B65D 75/00* (2006.01)
*A61L 9/12* (2006.01)
*A61L 2/18* (2006.01)
*C01B 11/02* (2006.01)

(52) U.S. Cl.
CPC ............... *A61L 2/20* (2013.01); *A61L 2/18* (2013.01); *A61L 9/127* (2013.01); *A61L 2202/11* (2013.01); *C01B 11/024* (2013.01)

(58) Field of Classification Search
CPC ............................. A61L 2/20; B65D 75/5866
USPC ........................................................ 422/123
See application file for complete search history.

(56) References Cited

U.S. PATENT DOCUMENTS

| 6,764,661 | B1 | 7/2004 | Girard |
| 8,361,409 | B2 | 1/2013 | Rico et al. |
| D676,949 | S | 2/2013 | Dornau et al. |
| 9,078,939 | B2 | 7/2015 | Dornau et al. |
| 2009/0142235 | A1 * | 6/2009 | Rico ...................... A01N 37/16 422/129 |

FOREIGN PATENT DOCUMENTS

| NZ | 286110 | * | 8/1998 |
| WO | 2007040588 | A1 | 4/2007 |

* cited by examiner

*Primary Examiner* — Kevin Joyner
*Assistant Examiner* — Holly M Mull
(74) *Attorney, Agent, or Firm* — Christopher & Weisberg, P.A.

(57) ABSTRACT

A disinfectant device including a pouch, the pouch including a first layer of material coupled to a second layer of material and defining a compartment therebetween. At least one dry reactant is retained within the compartment, the at least one dry reactant producing chlorine dioxide gas when exposed to water. A wick is at least partially disposed within the compartment. At least one from the group consisting of the first layer of material and the second layer of material define an array of ports along a periphery of the pouch and an array of fluid conduits, the array of fluid conduits being proximal to the array of ports, offset from the array of ports, in fluid communication with the wick, the compartment, and the array of ports.

10 Claims, 5 Drawing Sheets

DISINFECTANT POUCH WITH FLUID CONTROL

CROSS-REFERENCE TO RELATED APPLICATION

N/A

FIELD

The present technology is generally related to relate to a method and device for disinfection and deodorizing a volume of space, and in particular, a method and device for deodorizing a gas having integrated fluid uptake control.

BACKGROUND

The most common system and method for delivering disinfectants to surfaces, for example, tile, wood, granite, plastic, and glass is through the use of spray bottles containing a disinfectant solution. The user operates the spray bottle by aiming the bottle's nozzle in the direction of the surface to be treated and applying pressure to a trigger or pump sprayer which causes the release of the disinfectant in a small particle fluid form. However, because fluids from spray bottles have varied spray patterns, are dispersed as a mist, and rely on the precise aim of the user, portions of surfaces may remain untreated and therefore potentially infected with pathogens or materials causing noxious malodors.

To address airborne odors, bacteria, mold, and viruses, aerosols have been utilized to disinfect and deodorize the ambient air in an enclosed area, such as in a home, car, or cabin on a boat or plane. The dispersal of the fluid from canister or bottle may be achieved by repeated plunging of a lever that sprays a predetermined amount of fluid, or alternatively, the canister may continuously spray fluid so long as the plunger is depressed. However, similar to surface disinfectants, aerosol disinfectant delivery systems can only deliver disinfectant for a limited time and to a limited area. While gases from aerosols may substantially fill an area by entropic forces, because disinfectant gases from aerosols are not constantly released they are not effective at disinfecting substantially entire spaces evenly and rapidly.

Another method and system of deodorizing room may include providing plug-in or wall mounted units defining a reservoir that releases deodorizing particles. Drawbacks of such systems include, limited portability, as some units require electricity to operate; limited operability, as some units are motion activated; a predetermined rate of disinfectant release, as the disinfectant is released at a constant rate, and as a result, are of limited effectiveness, as none of the units on the market provide for both rapid release and slow release of gaseous disinfectant particles to sanitize a particular space.

SUMMARY

The techniques of this disclosure generally relate to a method and device for disinfection and deodorizing a volume of space.

In one aspect, the present disclosure provides a disinfectant device including a pouch, the pouch including a first layer of material coupled to a second layer of material and defining a compartment therebetween. At least one dry reactant is retained within the compartment, the at least one dry reactant producing chlorine dioxide gas when exposed to water. A wick is at least partially disposed within the compartment. At least one from the group consisting of the first layer of material and the second layer of material define an array of ports along a periphery of the pouch and an array of fluid conduits, the array of fluid conduits being proximal to the array of ports, offset from the array of ports, in fluid communication with the wick, the compartment, and the array of ports.

In another aspect, the first layer of material and the second layer of material are impermeable to water and permeable to gas.

In another aspect, each port in the array of ports is the same size and spaced equidistant from an adjacent port in the array of ports.

In another aspect, each conduit in the array of fluid conduits is the same size and spaced equidistant from an adjacent conduit in the array of fluid conduits.

In another aspect, the array of fluid conduits includes fewer fluid conduits than ports in the array of ports.

In another aspect, a width of each port in the array of ports is larger than a width of each conduit in the array of fluid conduits.

In another aspect, each port in the array of ports defines a fluid pathway connecting each port with a corresponding fluid conduit, and wherein the fluid pathway defines a width less than the width each port in the array of ports and the width of each conduit in the array of fluid conduits.

In another aspect, each port in the array of ports is longitudinally spaced from an adjacent port in the array of ports.

In another aspect, each conduit in the array of fluid conduits is longitudinally spaced from an adjacent conduit in the array of fluid conduits.

In another aspect, the wick spans an entirety of the compartment.

In another aspect, the wick is affixed between the first layer of material and the second layer of material and spans an entirety of the pouch.

In one aspect, a method of disinfecting a volume of space including exposing at least one reactant to water, the at least one reactant producing chlorine dioxide gas and being disposed within a pouch. A first layer of material is coupled to a second layer of material and defines a compartment therebetween. At least one dry reactant is retained within the compartment, the at least one dry reactant producing chlorine dioxide gas when exposed to water. A wick is at least partially disposed within the compartment. At least one from the group consisting of the first layer of material and the second layer of material define an array of ports along a periphery of the pouch and an array of fluid conduits, the array of fluid conduits being proximal to the array of ports, offset from the array of ports, and in fluid communication with the wick, the compartment, and the array of ports.

In another aspect, exposing the at least one reactant to water includes submerging the pouch in a volume of water.

In another aspect, exposing the at least one reactant to water including inserting the array of ports within a portion of a moisture transfer agent, and hydrating the moisture transfer agent.

In another aspect, the volume of space includes one or more living plants.

In another aspect, a width of each port in the array of ports is larger than a width of each fluid conduit in the array of fluid conduits.

In another aspect, each port in the array of ports defines a fluid pathway connecting each port with a corresponding fluid conduit, and wherein the fluid pathway defines a width less than the width each port in the array of ports and the width of each fluid conduit in the array of fluid conduits.

In another aspect, the wick spans an entirety of the compartment.

In another aspect, the wick is affixed between the first layer of material and the second layer of material and spans an entirety of the pouch.

In one aspect, a disinfectant device includes a pouch. The pouch includes a first layer of material coupled to a second layer of material and defining a compartment therebetween. At least one dry reactant is retained within the compartment, the at least one dry reactant producing chlorine dioxide gas when exposed to water. A wick is at least partially disposed within the compartment. At least one from the group consisting of the first layer of material and the second layer of material define an array of ports along a periphery of the pouch and an array of fluid conduits, the array of fluid conduits being proximal to the array of ports, offset from the array of ports, and in fluid communication with the wick, the compartment, and the array of ports. A width of each port in the array of ports is larger than a width of each fluid conduit in the array of fluid conduits, and each port in the array of ports defines a fluid pathway connecting each port with a corresponding fluid conduit, and the fluid pathway defines a width less than the width each port in the array of ports and the width of each fluid conduit in the array of fluid conduits/ The wick is affixed between the first layer of material and the second layer of material and spans an entirety of the pouch and divides the pouch into two equal halves.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
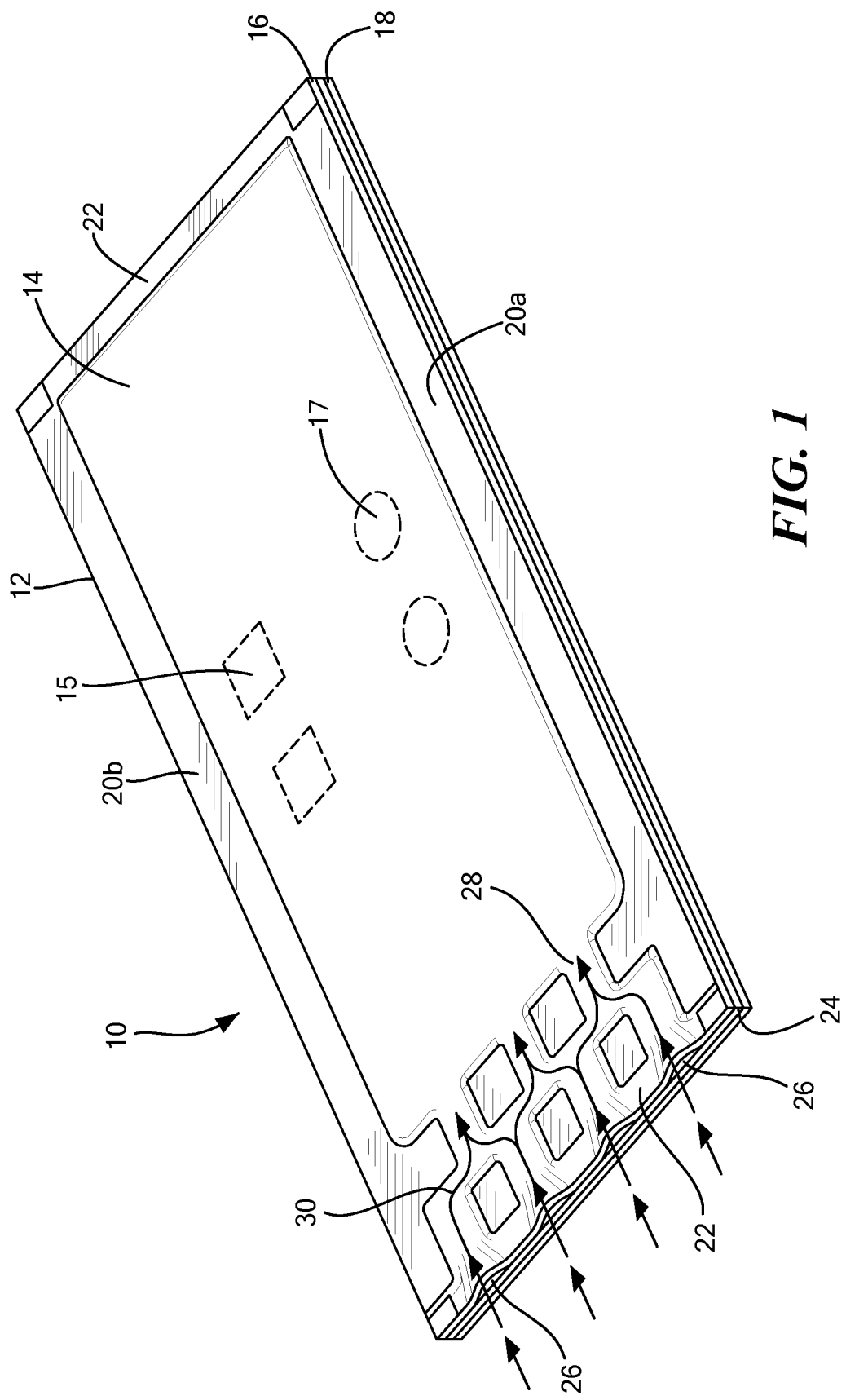
FIG. 1 is a front perspective view of a disinfectant device constructed in accordance with the principles of the present application.
Figure 2:
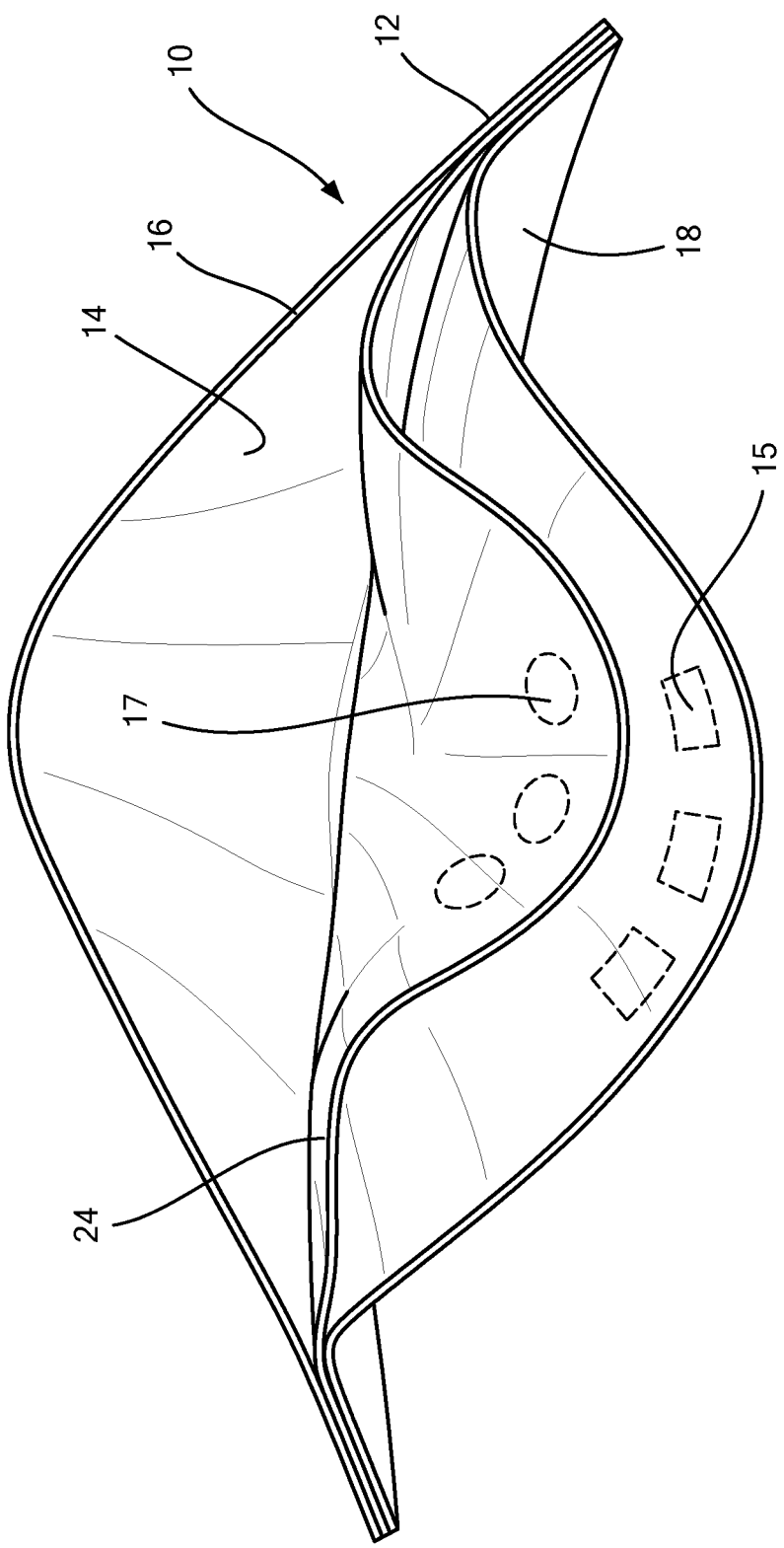
FIG. 2 is a front view of the device shown in FIG. 1 with an end removed to show a wick inside of a compartment.

Referring now to the drawings in which like reference designators refer to like elements there is shown in FIGS. 1 and 2 an exemplary disinfectant device constructed in accordance with the principles of the present application and designated generally as "10." The device 10 may include a pouch 12 sized and configured to retain the various components of the device 10 described herein. The pouch 12 may include one or more compartments 14 for retaining a first disinfectant reactant 15 in dry form, for example, power, pellets, flakes, granules, or solid tablets, configure to produce chlorine dioxide gas when exposed to water. In one configuration, the device 10 includes a first layer of material 16 affixed to a second lateral of material 18 along their respective edges to define the pouch 12 having one compartment 14 therebetween. For example, as shown in FIGS. 1 and 2, the first layer of material 16 is shown sealed along an its edges 20a and 20b which defines at least a portion of the periphery 22 of the pouch 12. The compartment 14 is disposed between the edges 20a and 20ab. For example, as shown in FIG. 1, edges 20a and 20 are sealed together along the periphery 22, thus coupling the first layer of material 16 to the second layer of material 18. However, the between the edges 20a and 20b the first layer of material 16 is not coupled to the second layer of material 18 creating the compartment. FIG. 2 shows the compartment disposed between the edges 20a and 20b with an end of pouch 12 removed to show the inside of the compartment.

In an exemplary embodiment, the pouch 12 and/or the one or more compartments 14 may be permeable to gases and impermeable to the first disinfectant reactant 15 and water. In other words, vapor and gases may be released from the pouch 12, such as chlorine dioxide gas, but dry matter is retained within the compartment 14. Moreover, the first layer of material 16 and the second layer of material 18 may further be impermeable to water such that water/moisture is only transported into the compartment through prefabricated fluid pathways, discussed in more detail below. In an exemplary embodiment, the first reactant 15 is in powder form spread about the one or more compartments 14 to provide for a larger surface area to react with water. The first reactant 15 may be any compound, chemical, or polymer that reacts with a substance, for example, water, to produce a disinfecting vapor. For example, in an exemplary embodiment, the first reactant 15 may contain, in part, chlorite, which may release chlorine dioxide gas when exposed to moisture and/or water vapor. Exemplary dry reactants are disclosed in U.S. Pat. No. 8,361,409 the entirety of which are expressly incorporated herein by reference. A second reactant 17 may also disposed with the one or more compartments 14, the second reactant being different than the first reactant 15. The second reactant 17 may a fragrance releasing reactant such that in addition to the pouch 12 releasing a disinfecting vapor, it may also release a fragrance.

Continuing to refer to FIGS. 1 and 2, a wick 24 may be disposed between the first layer of material 14 and the second layer of material 18. In one configuration, the wick 24 is a moisture absorbing material and/or transfer element configured to transport water from outside of the pouch 12 to inside of the compartment 14. In one configuration, the wick 24, the first layer of material 16 and the second layer of material 18 are commensurate in size such that each is co-terminus on all edges of the pouch 12. In other configurations, the wick 24 may be sized to be commensurate in size with the compartment 14 and include portions along fluid pathways and ports, as discussed in more detail below. In the configuration shown in FIG. 2, the wick 24 divides the compartment 14 into two equal half portions. In one configuration, the first reactant 15 is retained within one portion of the compartment 14 and the second reactant 17 is retained within another portion of the compartment 14. In other configurations, the first and second reactants 15 and 17 may be each disposed in one or more portions of the compartment 14.

Referring back now to FIG. 1, the rate at which chlorine dioxide is released from the pouch 12 depends on the amount of moisture and/or water present surrounding and penetrating the pouch 12. In particular, the more water transported into pouch 10, the greater the increase in the rate of chlorine dioxide production. Thus, the rate at which disinfectant is released from the pouch 12 may be varied depending on the amount of water present in proximity and the rate it is transported into the pouch 12. To that of the first layer of material 16 or the second layer of material 18 may define an array of ports 26 along a portion of periphery 22 of the pouch 12 and an array of fluid conduits 28. In the configuration shown in FIG. 1, the array of fluid conduits 28 are disposed proximal to the array of ports 26 and are offset from the array of ports 26. The array of fluid conduits 28 are in fluid communication with the wick 24, the compartment 14, and the array of ports 26. In the configuration shown in FIG. 1, each port in the array of ports 26 is a small opening between the first layer of material 16 and the wick 24 sized to allow water and moisture to enter and contact the wick 24. In other configurations, the array of ports 26 are openings formed between the second layer of material 18 and the wick 24 or both the first layer of material 16 and the second layer of material 18 to provide ports on both sides of the wick 24. In one configuration, each port in the array of ports 26 may be the same size and spaced equidistant from an adjacent port in the array of ports 26. Moreover, each conduit in the array of fluid conduits 28 may be the same size and be spaced equidistant from an adjacent conduit in the array of fluid conduits. It is contemplated, however, that the array of ports 26 and the array of fluid conduits 28 may include any number of ports and conduits of the same or different sizes and each port 26 and conduit 28 may be spaced at non-uniform distances away from each other. In one configuration, each port in the array of ports 26 is longitudinally spaced from an adjacent port in the array of ports and each conduit in the array of fluid conduits is longitudinally spaced from an adjacent conduit in the array of fluid conduits 28.

In one configuration, the number of fluid conduits in the array of the fluid conduits 28 is less than the number of ports in the array of ports 26 and are narrower to increase the velocity of water into the compartment 14. Moreover, the array of fluid conduits 28 being offset from the array of fluid ports 26 creates a fluid pathway 30 connecting each port with a corresponding fluid conduit. For example, as shown in FIG. 1, the fluid pathway 30 defines a width less than the width each port in the array of ports and the width of each conduit in the array of fluid conduits 28. In the configuration shown in FIG. 1, the fluid pathway 30 substantially spans the width of the array of the fluid ports 26 and is narrower than the array of fluid conduits 28 and is orthogonal to both the array of fluid ports 26 and the array of fluid conduits 28.

Figure 3:
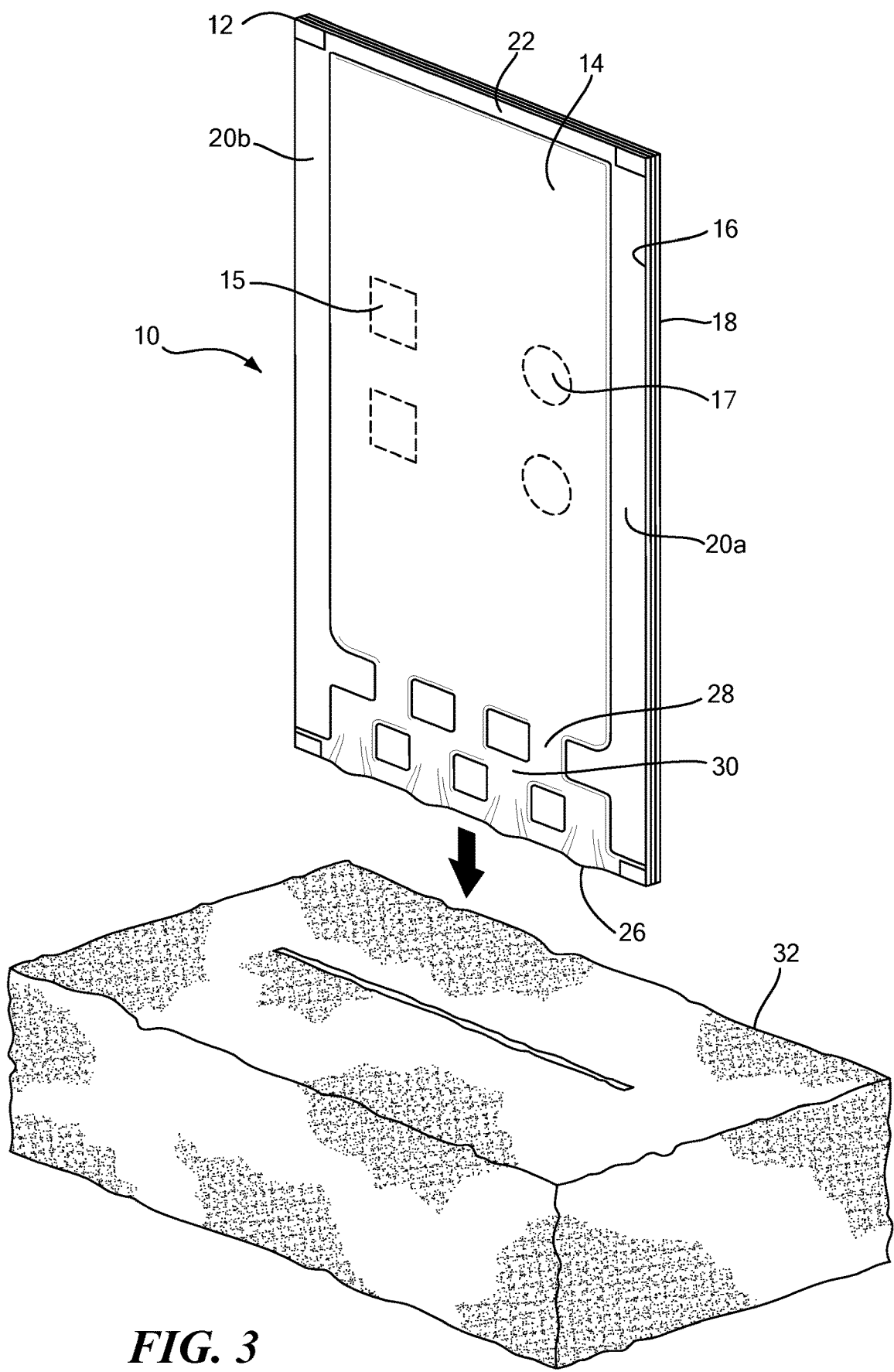
FIG. 3 is a perspective of the disinfectant device shown in FIG. 1 being inserted into a moisture absorbing element.
Figure 4:
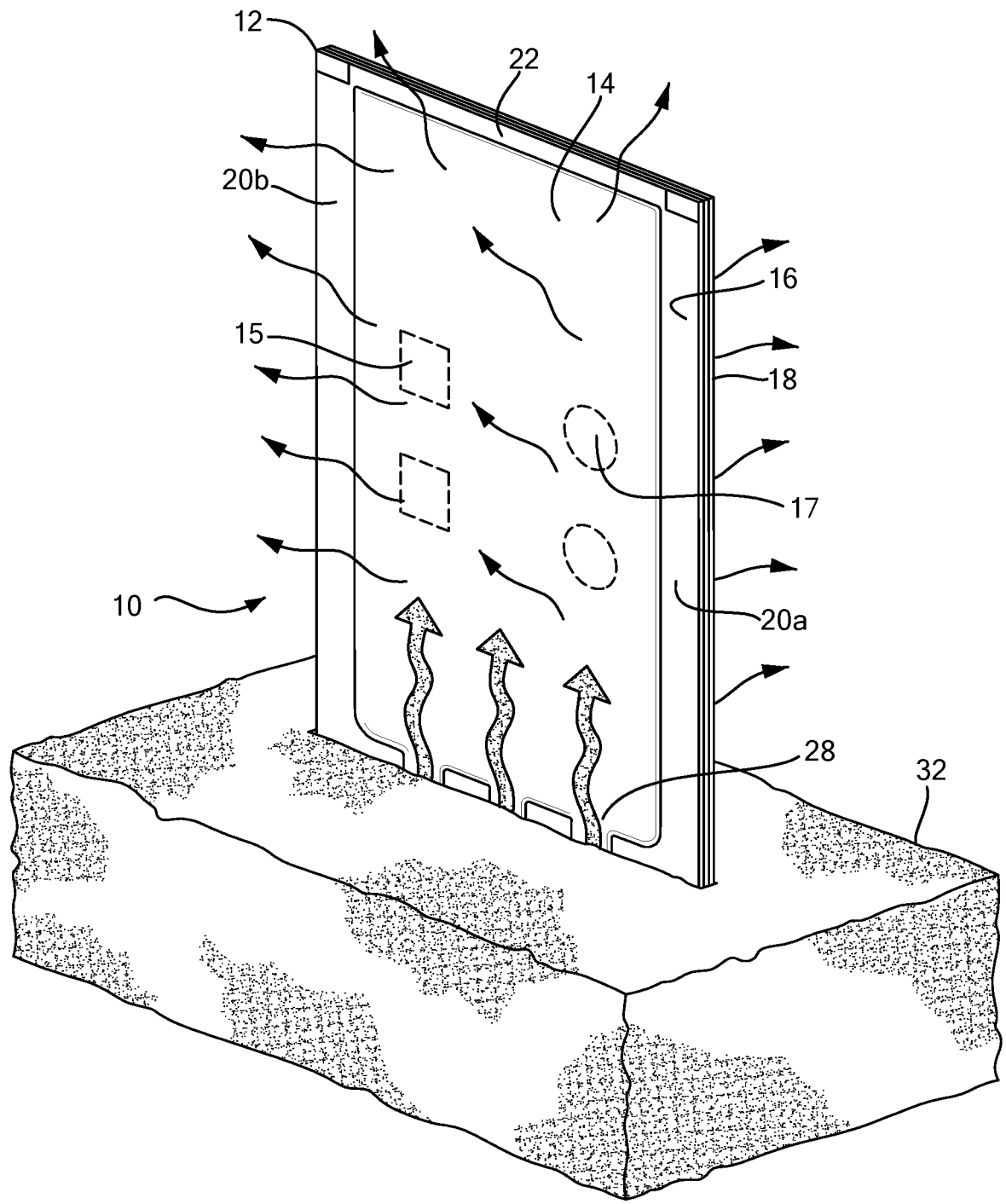
FIG. 4 is a perspective of the disinfectant device shown in FIG. 3 disposed within the moisture absorbing element and releasing a gas.

Referring now to FIGS. 3-4, in an exemplary use of the device 10, the pouch 12 may be removeably insertable within a moisture absorbing/transfer element 32, for example, a sponge, cloth, or other wicking material. Additional details about the sizing of the moisture absorbing element 32 may be found in U.S. Pat. No. 9,078,939, the entirety of which is expressly incorporated herein by reference. In the configuration shown in FIG. 3, the portion of the pouch 12 containing the array of fluid ports 26 is inserted within a slit of a wetted or otherwise hydrated sponge to transfer water into the compartment 14 of the pouch 12 to begin the reaction of creating chlorine dioxide gas. The size of the array of ports 26, the array of fluid conduits 28, and the width of the fluid pathway 30 may each vary to provide for a predetermined flow rate of fluid into the compartment 14 and thereby the rate at which chlorine dioxide gas is produced. For example, in one configuration, the array of ports 26 and/or the array of the fluid conduits 28 are sized such that approximately 100 PPM of chlorine dioxide gas is released after about 10-15 minutes of being exposed to water in the moisture transfer element 32.

Figure 5:
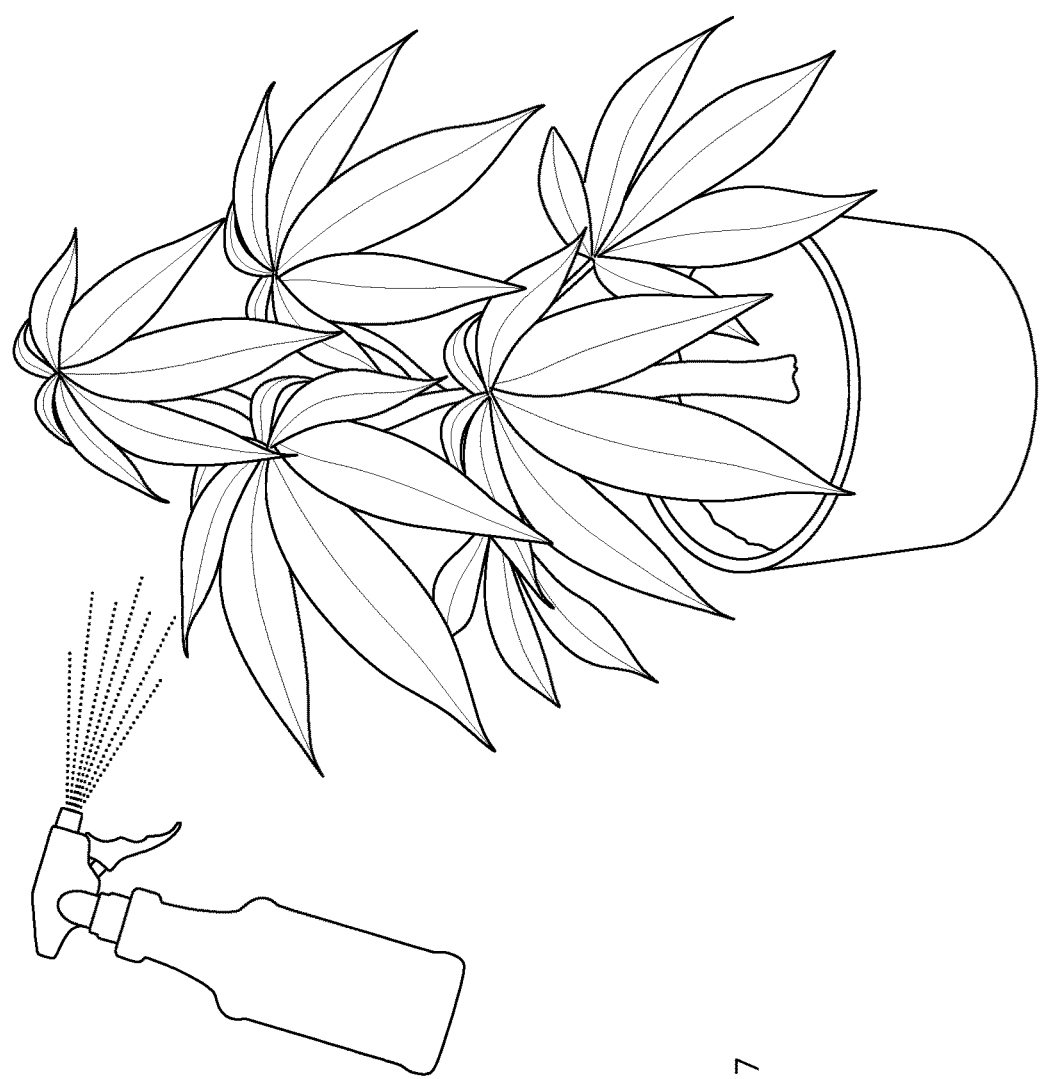
FIG. 5 is a cross-sectional view showing the disinfectant device shown in FIG. 1 being disposed in a container of water.
Figure 5:
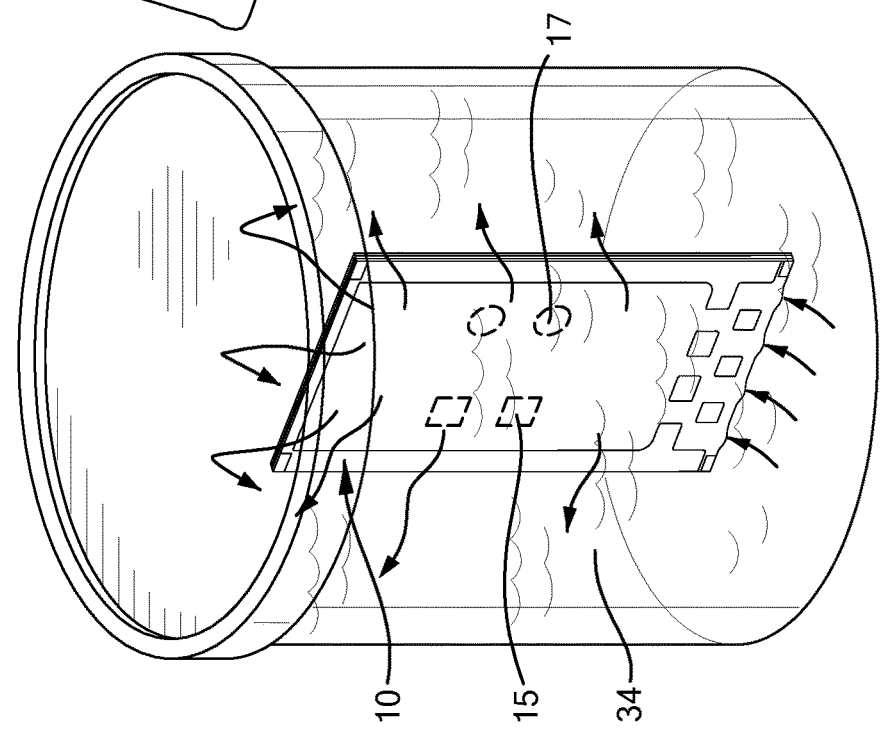

Referring now to FIG. 5, in another exemplary use, one or more pouches 12 may be submerged or otherwise deposited within a volume of water or aqueous solution to release a predetermined amount of chlorine dioxide into an aqueous solution. For example, depending on the desired concentration of chlorine dioxide, the number of pouches 12 to be deposited within a volume of water, for example, a bucket 34, may vary to produce a sufficient volume of chlorine dioxide, for example 100 ppm. In an exemplary use, a pouch 12 is inserted within a bucket 34 of water and a lid is closed around the bucket 34 which causes the CLO2 has to dissolve into solution as the bucket 34 is sealed. The solution may then be poured into a spray bottle or other liquid distribution device of treatment of a volume of space or material. In other configurations, a sprayer is attached directly to the bucket 34 to disperse the solution with CLO2. In particular, chlorine dioxide may be used to treat organic material, such as *Cannabis* plants in a grow house to prevent the formation of mold and mildew on the leaves.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A disinfectant device, comprising:
   a pouch, the pouch including a first layer of material coupled to a second layer of material and defining a compartment therebetween;
   at least one dry reactant retained within the compartment, the at least one dry reactant producing chlorine dioxide gas when exposed to water;
   a wick at least partially disposed within the compartment; and
   at least one from the group consisting of the first layer of material and the second layer of material defining an array of ports along a periphery of the pouch and an array of fluid conduits, the array of fluid conduits being:
   proximal to the array of ports;
   offset from the array of ports; and
   in fluid communication with the wick, the compartment, and the array of ports;
   a width of each port in the array of ports is larger than a width of each conduit in the array of fluid conduits, each port in the array of ports defines a fluid pathway connecting each port with a corresponding fluid conduit, the fluid pathway defining a width less than the width each port in the array of ports and the width of each conduit in the array of fluid conduits.

2. The device of claim 1, wherein the first layer of material and the second layer of material are impermeable to water and permeable to gas.

3. The device of claim 1, wherein each port in the array of ports is the same size and spaced equidistant from an adjacent port in the array of ports.

4. The device of claim 1, wherein each conduit in the array of fluid conduits is the same size and spaced equidistant from an adjacent conduit in the array of fluid conduits.

5. The device of claim 1, wherein the array of fluid conduits includes fewer fluid conduits than ports in the array of ports.

6. The device of claim 1, wherein each port in the array of ports is longitudinally spaced from an adjacent port in the array of ports.

7. The device of claim 1, wherein each conduit in the array of fluid conduits is longitudinally spaced from an adjacent conduit in the array of fluid conduits.

8. The device of claim 1, wherein the wick spans an entirety of the compartment.

9. The device of claim 8, wherein the wick is affixed between the first layer of material and the second layer of material and spans an entirety of the pouch.

10. A disinfectant device, comprising:
 a pouch, the pouch including a first layer of material coupled to a second layer of material and defining a compartment therebetween;
 at least one dry reactant retained within the compartment, the at least one dry reactant producing chlorine dioxide gas when exposed to water;
 a wick at least partially disposed within the compartment; and
 at least one from the group consisting of the first layer of material and the second layer of material defining an array of ports along a periphery of the pouch and an array of fluid conduits, the array of fluid conduits being:
 proximal to the array of ports;
 offset from the array of ports; and
 in fluid communication with the wick, the compartment, and the array of ports;
 a width of each port in the array of ports is larger than a width of each fluid conduit in the array of fluid conduits, and each port in the array of ports defines a fluid pathway connecting each port with a corresponding fluid conduit, and wherein the fluid pathway defines a width less than the width each port in the array of ports and the width of each fluid conduit in the array of fluid conduits; and
 the wick is affixed between the first layer of material and the second layer of material and spans an entirety of the pouch and divides the pouch into two equal halves.

* * * * *